United States Patent [19]

Tachibana et al.

[11] Patent Number: 5,582,586
[45] Date of Patent: Dec. 10, 1996

[54] DRUG ADMINISTRATION AND HUMOR SAMPLING UNIT AND AN APPARATUS THEREFOR

[76] Inventors: Katsuro Tachibana; Shunro Tachibana, both of 6-18, Kusagae 1-chome, Chuo-ku, Fukuoka-shi, Fukuoka 810, Japan

[21] Appl. No.: 232,002

[22] PCT Filed: Sep. 26, 1993

[86] PCT No.: PCT/JP93/01200

§ 371 Date: Apr. 22, 1994

§ 102(e) Date: Apr. 22, 1994

[87] PCT Pub. No.: WO94/05368

PCT Pub. Date: Mar. 17, 1994

[30] Foreign Application Priority Data

Aug. 28, 1992 [JP] Japan .................................. 4-230424

[51] Int. Cl.[6] .................................................. A61N 1/30
[52] U.S. Cl. ................... 604/20; 604/22; 601/2; 607/149; 128/760; 128/766
[58] Field of Search ........................ 604/20–22; 601/2; 607/149–153, 115; 128/760, 766

[56] References Cited

U.S. PATENT DOCUMENTS

| | | |
|---|---|---|
| 3,635,213 | 1/1972 | La Hay . |
| 3,794,910 | 2/1974 | Ninke et al. . |
| 4,457,748 | 7/1984 | Laltin et al. ............................. 128/760 |
| 4,821,740 | 4/1989 | Tachibana et al. ...................... 604/290 |
| 4,883,457 | 11/1989 | Sibalis .................................... 607/152 |
| 4,953,565 | 9/1990 | Tachibana et al. ....................... 604/20 |
| 5,115,805 | 5/1992 | Bommannan et al. .................... 604/20 |
| 5,279,543 | 1/1994 | Glikfeld et al. .......................... 604/20 |
| 5,282,785 | 2/1994 | Shapland et al. ......................... 604/20 |
| 5,291,887 | 3/1994 | Stanley et al. ........................... 128/760 |

FOREIGN PATENT DOCUMENTS

| | | |
|---|---|---|
| 3-170172 | 7/1991 | Japan . |
| 3170172 | 7/1991 | Japan ....................................... 604/20 |
| 0654254 | 3/1979 | U.S.S.R. .................................. 604/20 |
| 0931191 | 5/1982 | U.S.S.R. .................................... 601/2 |
| 1003853 | 3/1983 | U.S.S.R. .................................. 604/20 |
| 1103863 | 7/1984 | U.S.S.R. .................................. 604/20 |
| 1146059 | 3/1985 | U.S.S.R. .................................. 604/20 |
| 1648497 | 5/1991 | U.S.S.R. .................................. 604/20 |
| 91/12772 | 9/1991 | WIPO . |

OTHER PUBLICATIONS

"Development of TTS Drugs in the United States", Morimoto, Therapeutic Research, vol. 10, No. 3, 1989 (English Translation of relevant parts).

"Skinside Out", Scientific American, Nov. 1991, pp. 93–94.

*Primary Examiner*—John D. Yasko
*Assistant Examiner*—Mark Bockelman
*Attorney, Agent, or Firm*—Wilson Sonsini Goodrich & Rosati

[57] ABSTRACT

The present invention discloses a unit and its apparatus for drug administration and humor sampling, capable of increasing the drug absorption rate with a lower voltage applied and of collecting a sufficient amount of body fluid with a lower voltage applied. The present invention provides drug administration and humor sampling units A and B comprising electrodes 7a and 7b for applying D.C. voltage as well as ultrasonic vibrating elements 8a and 8b, each disposed inside fluid containers 4a and 4b having openings on the side for contact with skin and being filled with a solution; said drug administration and humor sampling units A and B being disposed on a common adhesive sheet 1 to form a drug administration and humor sampling apparatus. In accordance with this invention, as irradiation with ultrasonic waves reduces the electric resistance of the skin, sufficient electrical current will flow through the skin to enable drug administration or body fluid sampling by means of electrophoresis, even if the voltage between electrodes is reduced.

2 Claims, 7 Drawing Sheets

DRUG ADMINISTRATION AND HUMOR SAMPLING UNIT AND AN APPARATUS THEREFOR

This application is a 371 of PCT/JP93/01200 filed Aug. 26, 1993.

TECHNICAL FIELD

The present invention relates to a unit and apparatus for drug administration and humor sampling by using electrophoresis.

BACKGROUND ART

The treatment with percutaneous drug administration generally involves drugs in the form of a solution or ointment being applied to the skin to enable the drugs to be absorbed within their affected area. Although the absorption of the percutaneously applied drug is accomplished primarily through diffusion, the natural biophylaxic functions of the skin to prevent foreign matters such as medicines, microbes, and viruses from penetrating into the human body prevent most of the medicine from being absorbed. Furthermore, the absorption rate of the medicines that are successfully absorbed is made quite slow. There have been devised various methods for improving the absorption rate of drugs for the endermatic absorption.

One of the methods for improving the drug absorption rate is iontophoresis (iontophorese) described, for example, in MORIMOTO's "Development of TTS drugs in the United States," Therapeutic Research, Vol. 10, No. 3, 1989, pp. 169(889)–pp. 180(900).

Figure 9:
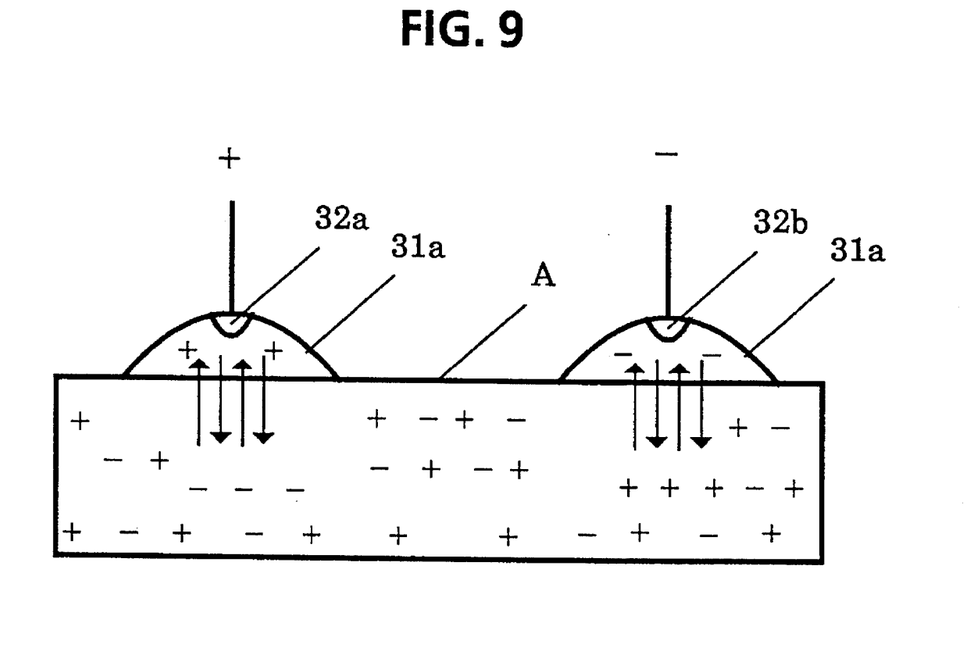
FIG. 9 is a schematic view indicating the principles of iontophoresis.

Iontophorese, namely iontophoresis, is a sort of electrotherapeutic method for introducing percutaneously or transmucosally predetermined medicines into a living body without pain by use of a direct current (refer to Nanzando's Medical Dictionary, published Apr. 10, 1974). As shown in FIG. 9, by providing electrodes $32a$ and $32b$ onto drug containers $31a$ and $31b$ and by providing the DC potential difference between respective electrodes $32a$ and $32b$, charged substances are transferred to within the skin A along with lines of the electrodynamic force. That is, positively charged substances will be attracted to the negative electrode $32b$ side, and negatively charged substances to the positive electrode $32a$ side. While transferring, the medicines will be absorbed into the bloodstream and transferred to whole body. Iontophoresis has the advantage of drug absorption being promoted, since, in addition to the effect of the concentration gradient, the drug may also be absorbed by the effect of electrophoresis.

As iontophorese sends an electric current through skin, if the resistance of the skin is increased, higher voltage must be applied to provide a sufficient current. This may cause low-temperature burning of the skin or patient discomfort. These problems may be avoided by lowering the applied voltage. In this case, however, the reduced amount of drug transfer by electrophoresis may not sufficiently increase the absorption rate of the drug. Furthermore, skin resistance may vary significantly with factors such as location, ambient conditions, perspiration, bloodstream, age and so on. As the quantity of the administered drug may differ among patients even when the same voltage is applied, this creates the disadvantage of stable drug administration being difficult to achieve.

The sampling of such humor as blood is performed for analyzing the patient's condition before treatment or for generic lab-testing. Usually, the sampling of body fluid is performed by using a syringe and a needle, which may cause pain as well as infection of the microbes. To overcome these difficulties, an attempt at aspirating body fluid out of body by applying heavy negative pressure onto the skin has been made. However, it is disadvantageous in that this attempt causes the subject pain when sucking and may leave a suction mark for a few days. Further problems are raised in that a large-scale device for generating the negative pressure may be required and its operation may be complicated.

Another method for sampling humor by electrophoresis as an application of above-mentioned iontophoresis is disclosed in "Skinside Out," Scientific American, November 1991, pp. 93–94. This attempt presents a problem in that a sufficient quantity of body fluid cannot be extracted using only electrophoresis. Although it may be possible to increase the current to extract more sampled humor, such problems as low-temperature burning and electric shock may result.

In Japanese Unexamined Patent Publication No. HEI-3-170172, a drug administration device using iontophoresis with the utility of ultrasonic wave vibration is disclosed. This drug administration device described in said Unexamined Patent Publication has been devised for administering drugs, and not for sampling body fluid. In addition, this drug administration device provides only one ultrasonic wave signal element on one of the electrodes for applying iontophoresis.

In International Patent Publication No. WO 91/12772, the use of iontophoresis technology after the irradiation of the skin with ultrasonic waves for the percutaneous drug administration is disclosed. There is not disclosed a point of simultaneously performing the ultrasonic wave irradiation method and iontophoresis method.

The object of the present invention is to provide a drug administration and humor sampling unit and its apparatus, which enables the drug absorption rate to be increased with lower applied voltage and is able to sample a sufficient quantity of body fluid with lower applied voltage.

DISCLOSURE OF THE INVENTION

The drug administration unit of the present invention is characterized in that electrodes for applying D.C. voltage and ultrasonic vibrating elements are provided on the inside of a container, said container having openings on the side for skin contact and being filled with a drug solution.

The humor sampling unit of the present invention is characterized in that electrodes for applying DC current and ultrasonic vibrating elements are provided on the inside of a container, said container having openings on the side for skin contact and being filled with an electrolyte solution.

Said container is allowed to connect to a connecting duct for infusing said solution into said container or for sampling said solution from said container.

Said electrodes can be disposed on the inner surface of the top plate of said container and said ultrasonic vibrating elements can be disposed at a position nearer said opening than said electrodes.

The drug administration apparatus or humor sampling apparatus may have mounted at least two of said drug administration units or humor sampling units onto a common adhesive sheet.

A driver device for applying respectively different DC potentials to each of the electrodes of said respective drug administration units or said humor sampling units as well as providing ultrasonic wave electric signals for each of said ultrasonic vibrating elements provided on said common adhesive sheet.

When administering the drugs within the container, they will be absorbed by the living body tissues through the epidermis by means of electrophoresis corresponding to the concentration gradient and the potential difference between electrodes. At the time of absorption, ultrasonic waves radiated on the area of percutaneous drug administration will lower the physical resistance by vibrating the skin and tissue of the irradiated area, and will consequently enable the drugs to easily penetrate the tissue and enable body fluids to easily exude near the skin surface. The ultrasonic vibration will eliminate some of the stratum corneum (horny layer) that comes off the skin surface and has the highest electric resistance, and the electrolyte solution of lower resistance will be diffused into the residual stratum corneum. The wetness of the skin surface and the removal of the high resistance portion of the skin surface will decrease the total resistance to allow the desired current to be kept at a low voltage. As the ultrasonic wave vibration may stabilize the significantly varying resistance of the horny layer of the skin surface at some lower level, the resistance of the skin may decrease to that of the intrinsic resistance of deep (dermal) skin, which is of smaller individual differences. Thus, the variation of electric currents provided for a given voltage will be decreased. Consequently, the desired dose of drugs will be stably administered. The ultrasonic wave also affects the drug being administered to improve its diffusion and dispersion. Further, the diffusion of the drug and the associated diffusion of water into the skin will decrease the electric resistance of the skin. Moreover, as the ultrasonic wave radiated onto the electrodes will prevent the polarization of the electrodes, the function of said electrodes may be sufficiently maintained. The ultrasonic wave vibration still prevents the polarization of the skin itself at the location to which voltage is applied.

When sampling humor, humor within living tissue will be extracted into the container by electrophoresis. The ultrasonic wave irradiation at that time will lower the physical and electric resistance of the skin to allow stable extraction of a sufficient quantity of body fluid with low voltage by improved extraction efficiency.

In accordance with the present invention, drug administration or humor sampling with a low voltage may be efficiently performed, since the physical and electric resistance of the skin may be reduced by the ultrasonic wave when administering drugs or sampling humor by electrophoresis. Since the voltage to be applied can be lowered, neither pain nor incongruity may hurt the subject, and a smaller battery can be used as a power supply. There is no need to apply heavily negative pressure for sampling body fluid, which may result in such inconveniences as suction marks on the skin, and no need to introduce a large-scale device for generating negative pressure. Further, the irradiation of ultrasonic waves will prevent polarization near the electrodes or in the skin, and drug administration or humor sampling may be performed with higher efficiency.

THE BEST MODE FOR CARRYING OUT THE INVENTION

The features of the present invention will be clearly described based on its preferred embodiment with reference to the accompanying drawings.

Figure 1:
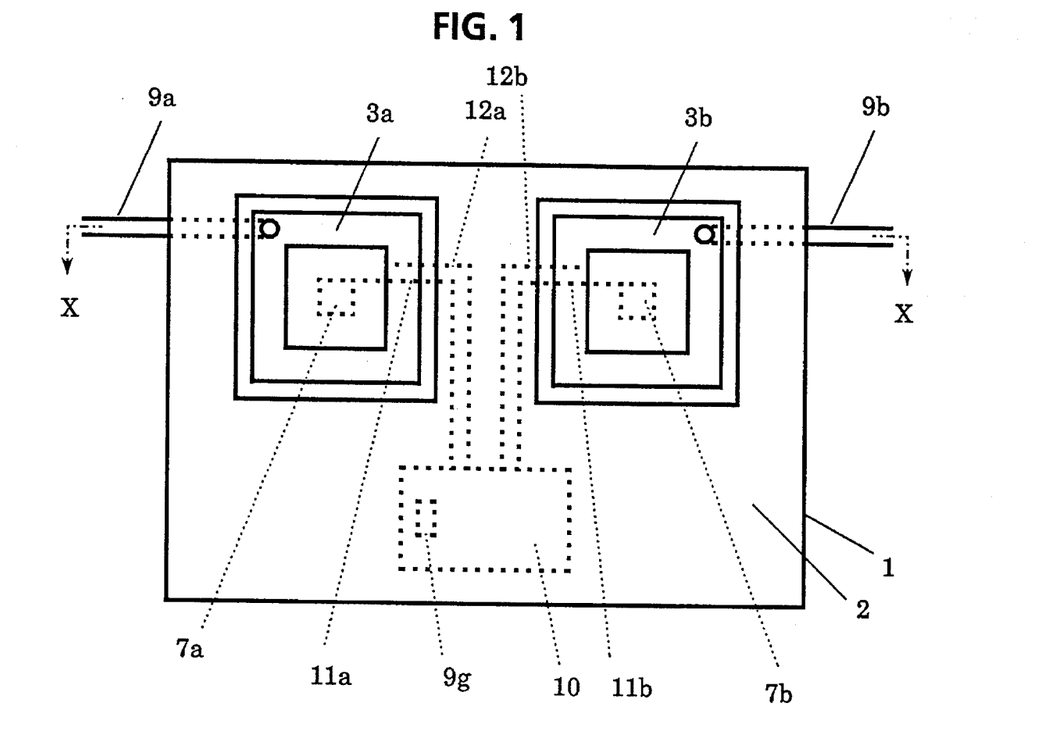
FIG. 1 is a bottom view of a preferred embodiment of the drug administration and humor sampling apparatus according to the present invention.
Figure 2:
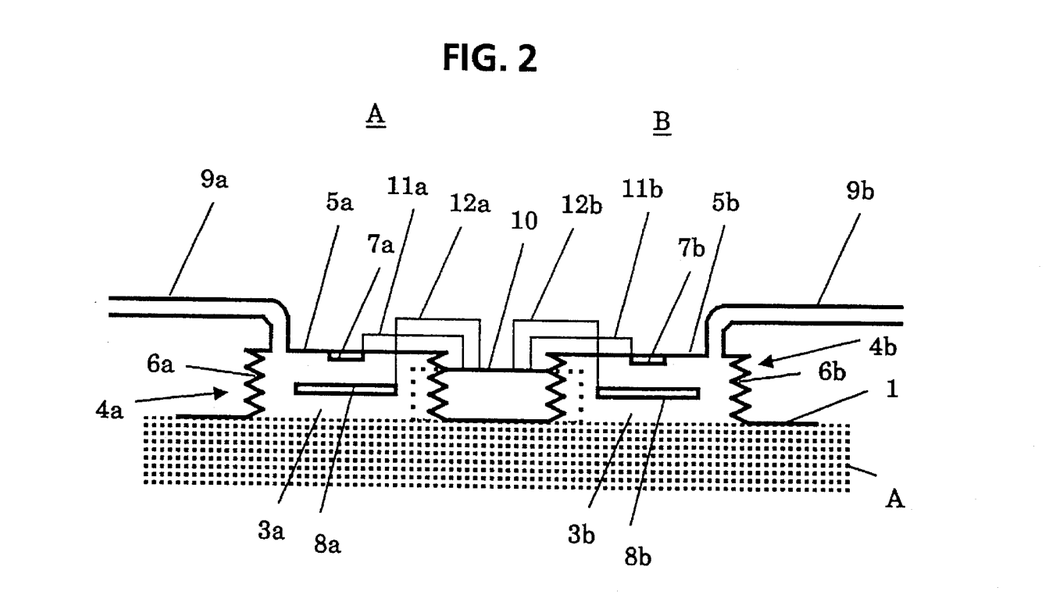
FIG. 2 is a sectional view of the drug administration and humor sampling apparatus of FIG. 1 along with the line X—X indicating the condition when pasting it to the skin.

FIG. 1 is a bottom view of a preferred embodiment of the drug administration and humor sampling apparatus according to the present invention. FIG. 2 is a sectional view of the drug administration and humor sampling apparatus of FIG. 1 along with line X—X indicating the condition when pasting it to the skin.

Referring to the drawings, reference numeral 1 designates an adhesive sheet comprising flexible synthetic resin. Some adhesive is applied to the bottom of this adhesive sheet 1 to form an adhesive surface 2. A detachable sheet (not shown) is attached to adhesive surface 2 before use of the drug administration and humor sampling apparatus. Adhesive sheet 1 has a plurality of (two in the case of the preferred embodiment) openings 3a and 3b formed therethrough, and liquid containers 4a and 4b integrated thereon to cover openings 3a and 3b. Liquid containers 4a and 4b are generally box-shaped, and comprise rectangular top plates 5a and 5b, and flexible components 6a and 6b in the form of bellows connecting the edges of top plates 5a and 5b to the edges of openings 3a and 3b with flexibility. Electrodes for applying DC voltage 7a and 7b are mounted to the inner surface of the top plates 5a and 5b of liquid containers 4a and 4b. These electrodes 7a and 7b are provided to be electrically exposed to the fluid in containers 4a and 4b. Rectangular planar ultrasonic vibrating elements 8a and 8b are disposed at a position below electrodes 7a and 7b. Ultrasonic vibrating elements 8a and 8b are structured with electrodes provided onto both sides of a piezoelectric material such as planar ceramics, and fluorine compound films. The electrodes of the ultrasonic vibrating elements 8a and 8b are arranged so as to be insulated from the fluid in containers 4a and 4b. Additionally, ultrasonic vibrating elements 8a and 8b are supported by supporting components not shown in the figure toward top plates 5a and 5b or flexible components 6a and 6b.

At top plates 5a and 5b of liquid containers 4a and 4b, flexible communication tubes 9a and 9b are connected and used for infusing drugs into or extracting fluid from liquid containers 4a and 4b. The tip of the communication tubes may be directly plugged into, or connected through removable coupling component to fluid supplier baths or fluid collector baths. Alternatively, by providing a plug capable of opening and closing for the tip of communication tubes 9a and 9b, the plug may be opened during the injection or extraction of fluid, and the plug may be closed during drug administration and humor sampling.

The drug administration and humor sampling units A and B comprise said containers 4a and 4b having openings 3a and 3b, and electrodes 7a and 7b for applying DC voltages and ultrasonic vibrating elements 8a and 8b both provided inside containers 4a and 4b. In this preferred embodiment, the drug administration and humor sampling units A and B are both mounted on a common adhesive sheet.

Where liquid containers 4a and 4b are not disposed in the upper side of the adhesive sheet 1 (the side opposed to adhesive surface 2), a driving device 10 is provided which is used for applying DC voltages to electrodes 7a and 7b and for supplying high frequency signals in the range of ultrasonic frequencies (referring to the ultrasonic signal below) to ultrasonic vibrating elements 8a and 8b.

Figure 3:
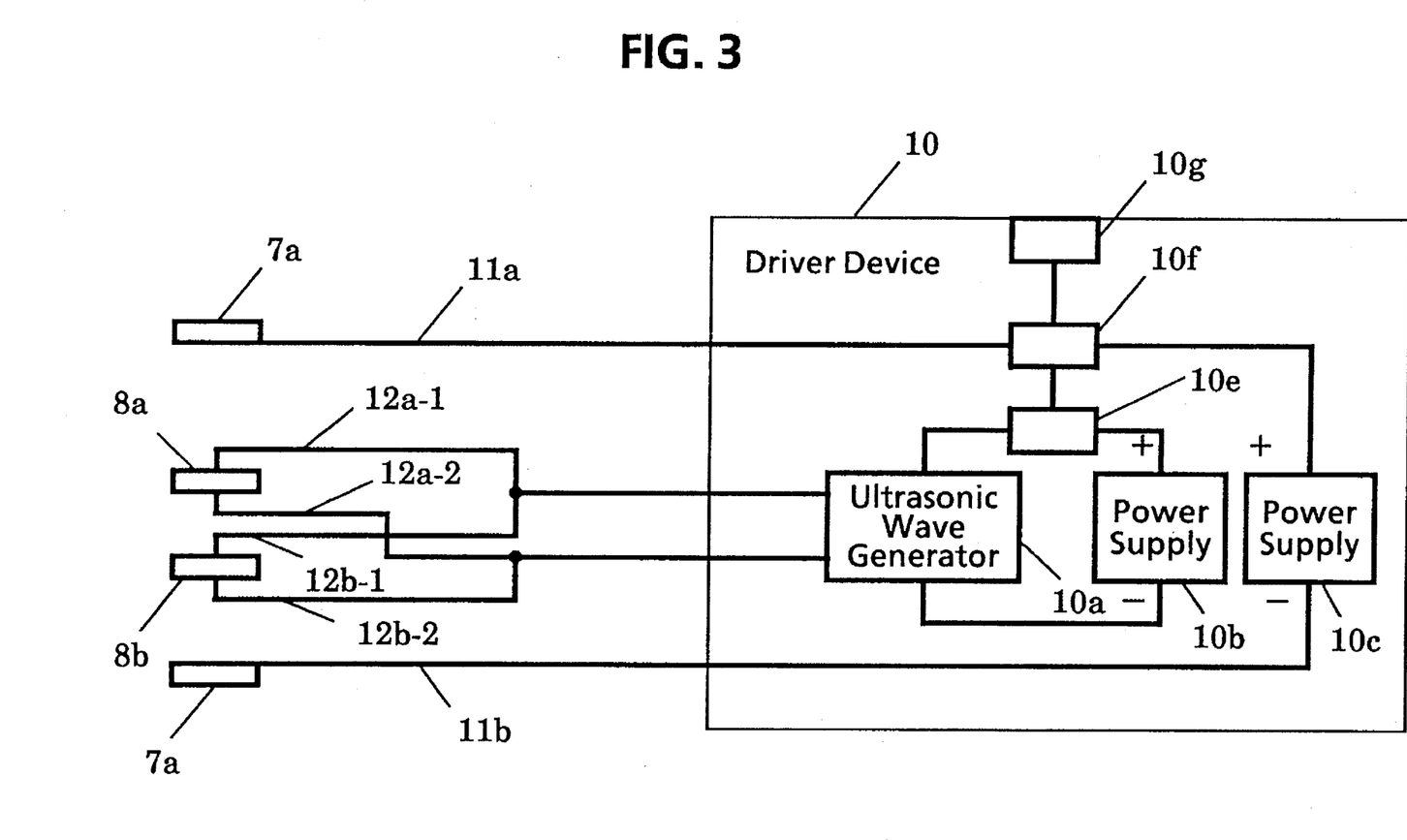
FIG. 3 is a schematic view showing the electric circuitry of the drug administration and humor sampling apparatus according to the present invention.

As shown in FIG. 3, there are disposed within driving device 10, an ultrasonic generating circuit 10a for generating ultrasonic electric signals and supplying a balanced output, a first power supply 10b for supplying the electrical current to operate ultrasonic generating circuit 10a by a battery or such, a second power supply 10c for providing the potential difference between electrodes 7a and 7b of liquid containers 4a and 4b, and so forth. Ultrasonic generating circuit 10a includes, for example, an ultrasonic oscillator circuit and an amplifier circuit for supplying ultrasonic electric signals from the oscillator circuit as a balanced output (both circuits are not shown). It should be noted that first power supply 10b and second power supply 10c are electrically isolated. Electronic switches 10e and 10f comprising transistors and the like are connected respectively to first power supply 10b and second power supply 10c to simultaneously turn on and off first power supply 10b and second power supply 10c by operating a power switch 10g provided so as to be exposed on the surface of driving device 10. It should be noted that a common power supply may be used instead of first power supply 10b and second power supply 10c, and in this case any transformer circuit may be used to step the voltage up or down to a desired regulating voltage.

Leads 11a and 11b for applying DC voltage are connected, from both electrodes 7a and 7b of said liquid container 4a and 4b, one lead 11a through electronic switch 10f to the positive terminal of second power supply 10c, another lead 11b directly to the negative terminal. From ultrasonic vibrating elements 8a and 8b, one pair of leads for each element for applying an ultrasonic electric signal, 12a-1, 12a-2, 12b-1, and 12b-2 is conducted respectively. Leads 12a-1 and 12b-1 are each connected to one of the output terminals of the ultrasonic generating circuit 10a in driving device 10, and leads 12a-2 and 12b-2 are connected to another output terminal of ultrasonic generating circuit 10a. The electrodes of ultrasonic vibrating elements 8a and 8b and leads 12a-1, 12a-2, 12b-1 and 12b-2 are clad by any appropriate electrically insulating materials so as to be electrically insulated from the fluid in containers 4a and 4b. In FIG. 1, leads 12a-1 and 12a-2 are bundled and shown as leads 12a, and leads 12b-1 and 12b-2 are bundled and shown as leads 12b.

Next, an aspect of operation when administering drugs by the above drug administration and humor sampling apparatus will be described.

First, a detachable sheet (not shown) has to be peeled off adhesive sheet 1 of the drug administration and humor sampling apparatus in order to expose adhesive surface 2, which is stuck to the skin of subject. Then, a liquid drug is injected into fluid containers 4a and 4b via communication tubes 9a and 9b. The flexible components can expand and shrink according to the dosage injected and liquid containers 4a and 4b will be filled with the desired dosage of drugs.

Then, power switch 10g is turned on. This causes both electronics switches 10e and 10f to turn on, and DC voltage to be applied between electrodes 7a and 7b. Ultrasonic generator circuit 10a also starts operating to supply an ultrasonic electric signal to ultrasonic vibrating elements 8a and 8b. As a result, ultrasonic waves are created from ultrasonic vibrating elements 8a and 8b and irradiated onto the skin A as well as the electrodes 7a and 7b.

By applying positive voltage to electrode 7a and negative voltage to electrode 7b, a series electric paths will be formed from electrode 7a through medicine, skin, body tissue, skin, and medicine to electrode 7b, and the DC current will flow along this same path. Positively charged substances within the drugs in one fluid container 4a will be attracted by the negative potential applied to electrode 7b, and move to the body tissue through skin A. In other words, the drugs are percutaneously injected by electrophoresis. Since ultrasonic waves generated from ultrasonic vibrating element 8a will be irradiating skin A at that time, the affected area of skin A will vibrate to lower the physical resistance, enable the drugs to easily penetrate into the body tissue, and allow body fluid to exude near the skin surface as well. Also, the ultrasonic vibration may cause the removal of the keratin layer from the skin surface, thereby removing the highest electric resistance, and the electrolyte solution of lower electric resistance penetrates and diffuses into the residual keratin layer. Because of the wet skin surface and the removal of the part of the skin with the highest resistance, the resistance on the whole will lower to allow the given electric current to be at a lower voltage. As the ultrasonic wave vibration may stabilize the significantly varying resistance of the horny layer of the skin surface at some lower level, the resistance of the skin may decrease to the intrinsic resistance of deep (dermal) skin of smaller individual difference, allowing the variation of the electric current for a given voltage to decrease. Consequently, the desired dose of drugs will be stably administered. Additionally, the ultrasonic wave also affects the drug being administered to improve its diffusion and dispersion. Moreover, the increased diffusion of the drug and its associated diffusion of water into the skin further decreases the electrical resistance of the skin.

Figure 4:
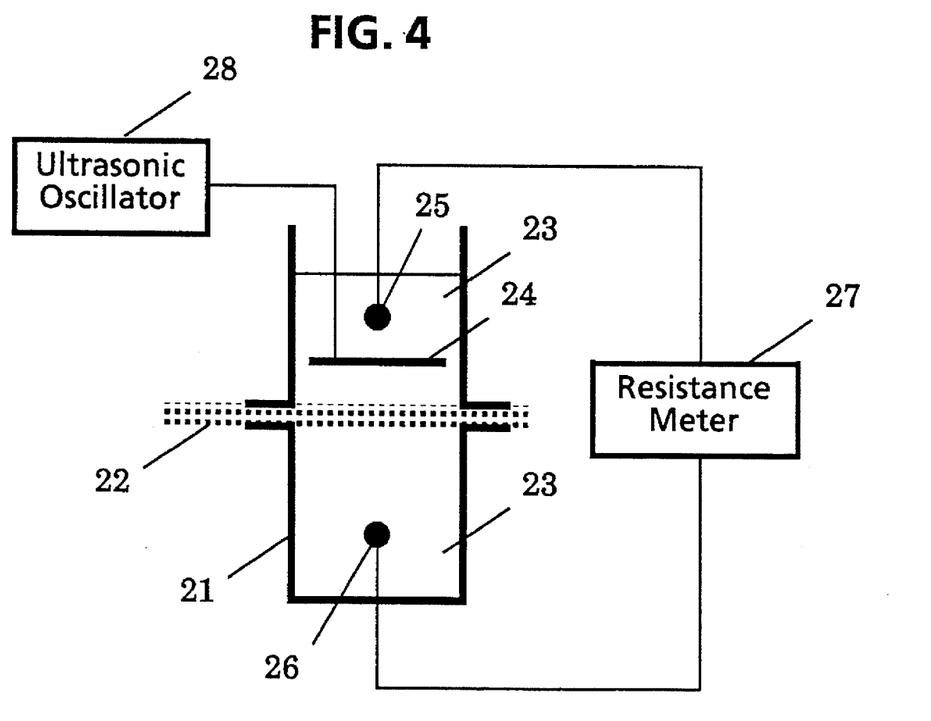
FIG. 4 is a schematic showing laboratory devices for observing the changes of electrical resistance of the skin when ultrasonic waves are radiated.

Now referring to FIG. 4, the laboratory examination performed for observing the change of dermal electrical resistance brought by ultrasonic irradiation will be described herein below.

[Method]

Skin was removed from hairless mice. A cylinder 21 of 3 cm diameter was divided by using the removed mouse skin for splitting it to two portions. The spaces on both sides of the skin 22 were filled with a saline 23. A planar ultrasonic vibration element 24 of 10 mm by 10 mm and an electrode for resistance measurement were disposed to the outside of the skin keratin layer, and a counter electrode 26 was disposed to the inside of the skin.

Skin resistance was measured by flowing square waves of pulse width of 500 ms per 10 seconds, and by the resistance between electrodes 25 and 26 across both sides of skin 22 through saline 23 by means of a resistance meter using a half bridge. The polarity of electrodes was negative on the outside of the skin. Additionally, ultrasonic electric signals of 22 V, 170 kHz were supplied from ultrasonic oscillator 28 to ultrasonic vibration element 24 to generate ultrasonic signals that would irradiate an ultrasonic wave toward skin 22. The method of ultrasonic irradiation used was the pulsing method in which a 3-second cycle of irradiation and a pause of 7 seconds iterates. The total irradiation period for one operation was 60 seconds including the pauses.

[Results]

Figure 5:
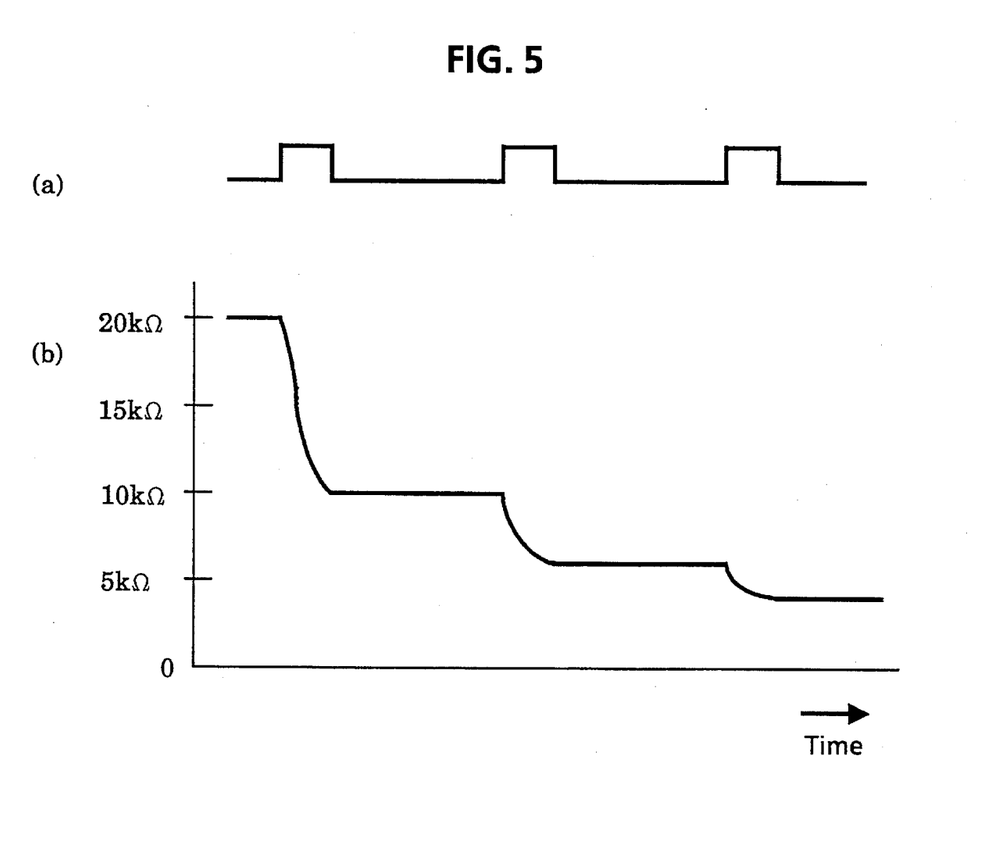
FIG. 5 is a graph indicating the decrease of electrical resistance of the skin when ultrasonic waves are radiated.

The resistance of the skin disposed in the saline without treatment was approximately 21 k-ohms one hour after removal. The change of skin resistance over 24 hours in the identical condition was observed and found to be stable. Conversely, when irradiated with ultrasonic pulses at the timing shown in FIG. 5a, skin resistance began to decrease just after the ultrasonic irradiation, and after 1 minute, it was reduced approximately 50% to 10 k-ohms. After that, by twice irradiating with an ultrasonic wave, skin resistance was reduced further to reach 6 k-ohms. The increased temperature due to ultrasonic irradiation during this experiment was less than 1 degree C. Observation 6 hours after the irradiation revealed that the reduced skin resistance held at the same level. Observation of the affected region of the skin after the experiment revealed that the region appeared completely the same as the non-irradiated region, and that there was no damage by ultrasonic waves. The resistance of skin with the keratin layer peeled mechanically with a needle was immediately reduced to 5 k-ohms.

As can be appreciated from the experiment above, a significant reduction of skin resistance by irradiating with an ultrasonic wave was confirmed.

The laboratory examination performed for observing the change of drug permeability by ultrasonic irradiation will be described herein below.

[Method]

Figure 6:
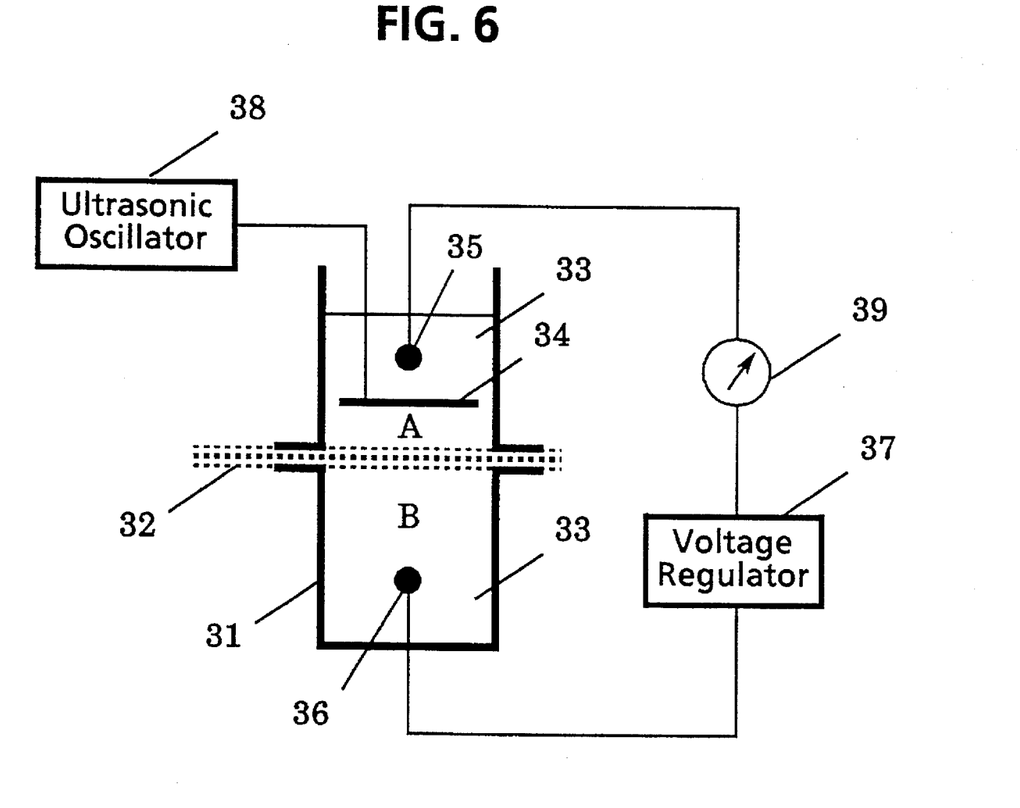
FIG. 6 is a schematic view showing laboratory devices for observing the changes of drug permeability when ultrasonic waves are radiated.

Skin was removed from hairless mice aged from 8 to 12 weeks. As shown in FIG. 6, a cylinder 31 of 3 cm diameter was divided using the removed mouse skin into two portions: cell A for the epidermis side of the skin, and cell B for the cutis side of the skin. In the cell A, a planar ultrasonic vibrating element 34 of 8 mm by 8 mm and an electrode for the cathode of iontophoresis were disposed. 5 ml of PBS (phosphate buffer solution) and the object drug of this experiment, 1 ml of PSP (phenolsulfophthalein) were infused into cell A. 15 ml of PBS was infused into cell B. Ultrasonic vibrating element 34 was appeared at 210 kHz, 1 watt/cm$^2$, and a voltage regulator 37 was used for adjusting voltages while measuring the electrical current by ammeter 39 for the iontophoresis to be with 0.35 mA at the beginning of the experiment. An ultrasonic oscillator 38 and a voltage regulator 37 were controlled by a computerized controller with iterative square waves of an "on" state lasting 3 seconds and an "off" state lasting 7 seconds, so as to synchronize the ultrasonic system and the iontophoresis system. The results were determined by sequentially measuring absorbance (O.D.) of the PSP concentration in cell B to compute drug permeability. Changes in the electrical current of iontophoresis were also recorded simultaneously with a polygraph (schematically shown as ammeter 39 in FIG. 6).

[Results]

Figure 7:
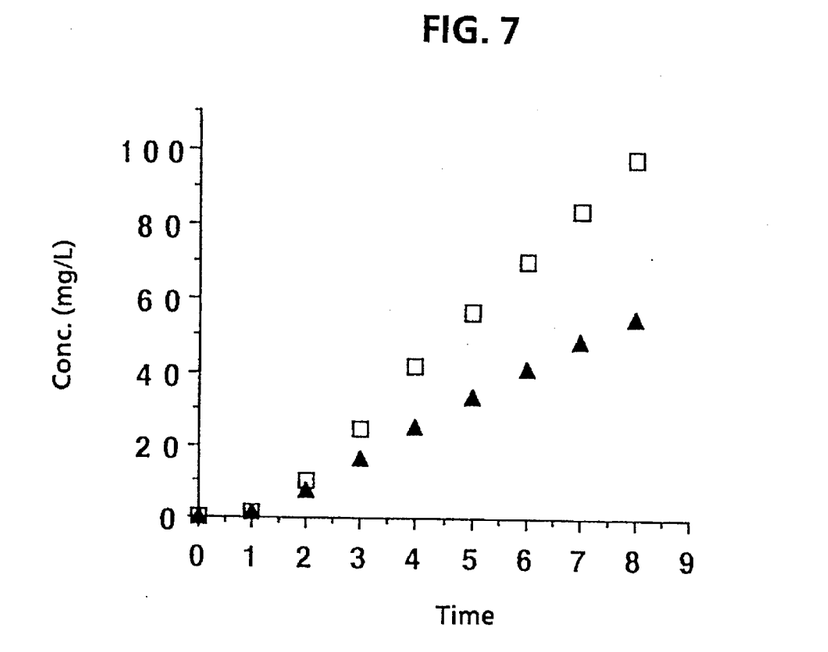
FIG. 7 is a graph indicating the changes of drug permeability when ultrasonic waves are radiated.
Figure 8:
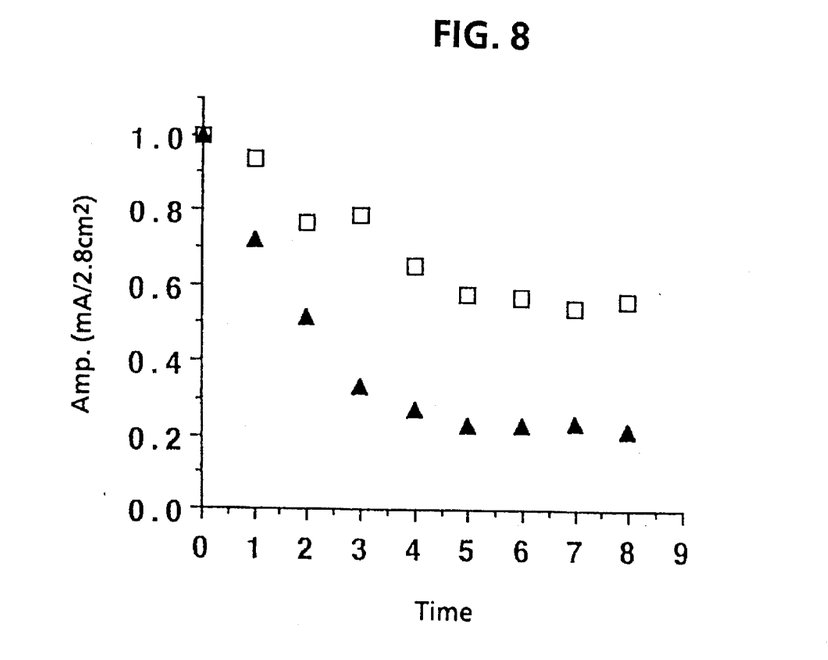
FIG. 8 is a graph indicating the changes of electrical current when ultrasonic waves are radiated.

In FIG. 7, a graph is shown indicating the results from the control (shown with triangular symbols) with iontophoresis only and from the subject (shown with square symbols) with two independent systems together and with ultrasonic waves operated simultaneously. Skin obtained from one hairless mouse was laterally split for both experiments. In this graph the ordinate shows PSP concentrations in cell B, and the abscissa shows time. The difference of PSP concentration had been obvious 2 hours after the beginning, then the rising rate of the subject was approximately twice that of the control thereafter. In FIG. 8, are shown the changes in the current of the control (shown with triangular symbols) and that of the ultrasonic subject (shown with square symbols) simultaneously measured in the same experiment. As shown in FIG. 8, the current was gradiently reduced from 1 mA to 0.6 mA in the subject with ultrasonic treatment, while it was rapidly decreased from 1 mA to 0.2 mA in the control.

It was revealed in this experiment that the iontophoresis together with ultrasonic irradiation reinforced the ion penetrating effect.

As mentioned above, since DC voltage is applied to electrodes 7a and 7b which in turn polarize near their surface, the effect of drug injection by the potential difference may be reduced. In the preferred embodiment, however, as the ultrasonic waves are also radiated onto electrodes 7a and 7b, some micro-flow near the surface of electrodes 7a and 7b is generated, which will cancel the polarization and thus prevent reduction of the function of the electrodes. The polarization may appear not only on the surface of the electrodes but also inside the skin. This polarization inside the skin will be also prevented by the ultrasonic wave irradiation.

Medicines available for infusion with the drug administration and humor sampling apparatus of the present invention include: scopolamine, nitroglycerine, indomethacine, ketoprofen, carpronium chloride, insulin, various hormones, antibiotics, carcinostatics, antihypertensives, morphine, lidocaine, psychotropics, etc.

As mentioned above, when injecting drugs by electrophoresis with the drug administration and humor sampling apparatus of the present invention, stable administration of the desired dosage of medicines at a lower voltage will be provided by reducing the physical and electrical resistance of the skin with ultrasonic waves.

Next, another aspect of operation when sampling body fluids by using the above-mentioned drug administration and humor sampling apparatus will be described. The apparatus used will be the same as shown in FIG. 1 and 2.

First, as in the case of drug administration cited above, a detachable sheet (not shown) is peeled off adhesive sheet 1 of the drug administration and humor sampling apparatus to expose adhesive surface 2, and adhesive surface 2 of adhesive sheet 1 is stuck to the skin of the subject. Then, for sampling body fluid, a solution containing electrolytes such as Na, K, Cl, etc. (referring to "electrolytic solution" herein below) is to be infused into fluid containers 4a and 4b via communication tubes 9a and 9b. Then the power switch 10g is turn on. This causes DC voltage to be applied between electrodes 7a and 7b. The ultrasonic generator circuit 10a also starts operating to supply an ultrasonic electric signal to the ultrasonic vibrating elements 8a and 8b. Consequently, ultrasonic waves will be created from ultrasonic vibrating elements 8a and 8b and irradiated to skin A as well as to electrodes 7a and 7b.

By applying positive voltage to electrode 7a and negative voltage to electrode 7b, a series of electrical paths will be formed from electrode 7a through medicine, skin, body tissue, skin, and medicine to electrode 7b, and the DC current will flow along this same path. Positively charged substances within the body fluid of the living tissue in the area corresponding to one fluid container 4a will be attracted by the negative potential applied to the electrode 7b, and move to the electrolytic solution contained in fluid container 4a through skin A. In other words, body fluid is percutaneously collected by electrophoresis.

Since ultrasonic waves generated from ultrasonic vibrating element 8a will be irradiated onto skin A at that time, the affected area of skin A will vibrate to allow body fluids to exude near the skin surface and to lower the physical resistance to enable body fluid to be easily collected into fluid container 4a. Also, the ultrasonic vibration may cause the keratin layer to peel off the skin surface and, thus having the layer of highest electric resistance removed, an electrolyte solution of lower electrical resistance can penetrate and diffuse into the residual keratin layer. Because the skin surface becomes wet and the part of highest resistance on the skin surface is removed, the resistance on the whole will lower to allow the given electrical current to be of a at lower voltage. As the ultrasonic wave vibration may stabilize the significantly varying resistance of the horny layer of the skin surface at some lower level, the resistance of the skin may decrease to the level of the intrinsic resistance of deep (dermal) skin of smaller individual difference. Thus, the variation of the electric current for a given voltage will also decrease. As a result, body fluid may be sampled in a stable way. It should be noted that although body fluid moving into fluid container 4a may add the body fluid volume to the solution volume, the apparatus can cope with this additional volume by extending flexible component 6a of fluid container 4a.

Further, as in the case of drug administration, the reduced efficiency caused by the polarization of electrodes 7a and 7b as well as the skin can be avoided with ultrasonic irradiation.

Another fluid container 4b can collect positively charged substances of body fluid. The collecting mechanism is the same as that of container 4a.

Body fluid gathered in fluid container 4a and 4b together with the electrolytic solution can be taken out through communication tubes 9a and 9b for analysis of the contents such as enzymes, electrolytes, glucose in the bloodstream by using well-known means of component analysis.

As mentioned above, when sampling body fluid by electrophoresis with the drug administration and humor sampling apparatus of the present invention, a stable sampling of the desired dosage of body fluid at a lower voltage will be provided by reducing the physical and electrical resistance of the skin with ultrasonic waves.

In the preferred embodiment, two sets of drug administration and body fluid sampling units are provided on one common adhesive sheet. However, each of the two units can be separately disposed on each of the two independent adhesive sheets, respectively.

Additionally, more than two drug administration and body fluid sampling units may be disposed on one common adhesive sheet. In this case, wiring to each of the electrodes and ultrasonic vibrating elements of a plurality of drug administration and body fluid sampling units may be provided in a parallel fashion.

Further, in the preferred embodiment described above, a driving device has been disposed on the common adhesive sheet. However, the driving device may be separately provided to apply voltage to each electrode via leading wires and connectors.

INDUSTRIAL AVAILABILITY

The present invention may be used in the field of clinical treatment and diagnosis of patients.

We claim:

1. A drug administration apparatus comprising a drug administration unit including an electrode for applying D.C. voltage and an ultrasonic vibrating element, each being disposed inside a common container positioned on an adhesive sheet, said container having an opening on a side adjacent to said adhesive sheet for contacting skin and said container being filled with a drug solution wherein at least two of said drug administration units are disposed on said adhesive sheet, said apparatus further comprising a driving device disposed on said adhesive sheet for applying different DC potentials to each of the electrodes of said respective drug administration units and for providing ultrasonic wave electric signals for each of said ultrasonic vibrating elements.

2. A humor sampling apparatus comprising a humor sampling unit including an electrode for applying D.C. voltage and an ultrasonic vibrating element, each being disposed inside a common container positioned on an adhesive sheet, said container having an opening on a side adjacent to said adhesive sheet for skin contact and said container being filled with an electrolytic solution wherein at least two of said humor sampling units are disposed on said adhesive sheet, said apparatus further comprising a driving device disposed on said adhesive sheet for applying different DC potentials to each of the electrodes of said respective humor sampling unit and for providing ultrasonic wave electric signals for each of said ultrasonic vibrating elements.

\* \* \* \* \*